United States Patent
Huang

[11] Patent Number: 6,044,848
[45] Date of Patent: Apr. 4, 2000

[54] TOOTHPICK ASSEMBLY

[76] Inventor: Pin-Chin Huang, P.O. Box 82-144, Taipei, Taiwan

[21] Appl. No.: 09/240,663

[22] Filed: Feb. 2, 1999

[51] Int. Cl.[7] .......................... A61C 15/00; A24F 27/00; B65D 69/00
[52] U.S. Cl. .......................... 132/321; 132/329; 206/104; 206/581; 206/113
[58] Field of Search .................... 132/321, 329, 132/328, 323; 206/63.5, 102, 473, 474, 581, 104, 113

[56] References Cited

U.S. PATENT DOCUMENTS

| | | | |
|---|---|---|---|
| 791,638 | 6/1905 | Metzger | 206/63.5 |
| 808,606 | 12/1905 | Helmel | 206/63.5 |
| 1,382,459 | 6/1921 | Bercovici | 206/63.5 |
| 1,586,918 | 6/1926 | Sakowski | 206/63.5 |
| 1,856,559 | 5/1932 | Johnson | 206/63.5 |
| 2,111,265 | 3/1938 | Heckel | 206/63.5 |
| 2,760,628 | 8/1956 | Briggs | 206/29 |
| 2,762,501 | 9/1956 | Cameron | 206/29 |
| 5,119,941 | 6/1992 | Lepie | 206/102 |
| 5,415,276 | 5/1995 | Welton | 206/104 |
| 5,855,215 | 1/1999 | Clarke | 132/321 |

*Primary Examiner*—John J. Wilson
*Assistant Examiner*—Robyn K. Doan
*Attorney, Agent, or Firm*—A & J

[57] ABSTRACT

A toothpick assembly includes a rectangular plastic envelope having a rectangular bottom, a rectangular upper top panel, a rectangular lower top panel, a rectangular left panel formed with a slit, and a rectangular right panel formed with a tongue configured to fit in said slit, and six plastic toothpick sheets each having six toothpicks separated at an upper portion and joined together at a root portion, a breaking line being pressed between said upper portion and said root portion, said plastic toothpick sheets being stacked up and affixed to said bottom panel, whereby the toothpick assembly is convenient to carry and sanitary in use.

1 Claim, 7 Drawing Sheets

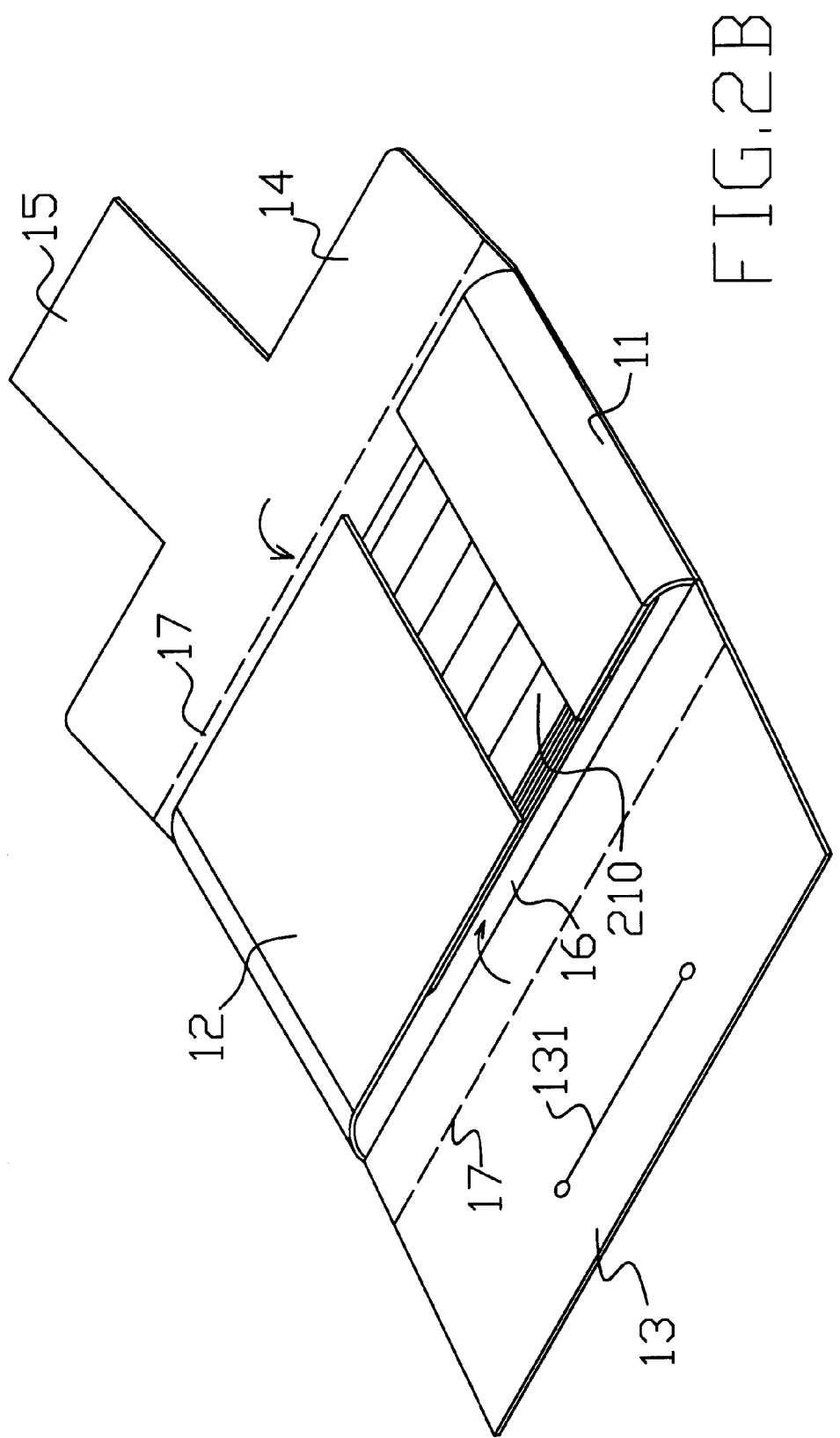

TOOTHPICK ASSEMBLY

BACKGROUND OF THE INVENTION

1. Field of the Invention

This invention is related to a toothpick assembly which is convenient to carry and sanitary in use.

2. Description of the Prior Art

The conventional tools for cleaning mouth are nothing more than toothpicks and dental floss picks, but their structure and package render them very inconvenient to carry (see FIG. 4). In addition, most of the toothpick sold on the market is made of bamboo which suffers from two drawbacks: 1. easy to become mildewed when dampened; 2. causing damage to the environment.

In addition, the toothpicks are arranged closed to each other in a container, so that when one takes a toothpick from the container, one's hand will be inevitable to touch and dirty other toothpicks. Furthermore, the toothpicks will easily drop out of the container if the container is not opened very carefully.

Regarding dental floss, it is necessary to open the mouth very wide in order to clean between teeth and so it is very difficult to use especially in cleaning between teeth at the rear portion of the mouth.

Therefore, it is an object of the present invention to provide an improved toothpick assembly which can obviate and mitigate the above mentioned drawbacks.

SUMMARY OF SAID INVENTION

This invention is related to an improved toothpick assembly.

According to the present invention, a toothpick assembly includes a rectangular plastic envelope having a rectangular bottom, a rectangular upper top panel, a rectangular lower top panel, a rectangular left panel formed with a slit, and a rectangular right panel formed with a tongue configured to fit in said slit, and six plastic toothpick sheets each having six toothpicks separated at an upper portion and joined together at a root portion, a breaking line being pressed between said upper portion and said root portion, said plastic toothpick sheets being stacked up and affixed to said bottom panel.

It is the primary object of the present invention to provide an improved toothpick assembly which is convenient to carry.

It is another object of the present invention to provide an improved toothpick assembly which can keep the toothpick in sanitary condition.

It is still another object of the present invention to provide an improved toothpick assembly which is safe in use.

It is still another object of the present invention to provide an improved toothpick assembly which can clean between teeth thoroughly.

It is a further object of the present invention to provide an improved toothpick assembly which can be firmly held by hand.

The foregoing objects and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts. Many other advantages and features of the present invention will become manifest to those versed in the art upon making reference to the detailed description and the accompanying sheets of drawings in which a preferred structural embodiment incorporating the principles of the present invention is shown by way of illustrative example.

BRIEF DESCRIPTION OF THE DRAWINGS

FIGS. 2A, 2B, 2C and 2D illustrates how to open and close the plastic envelope;

DETAILED DESCRIPTION OF THE PREFERRED EMBODIMENT

Figure 1:
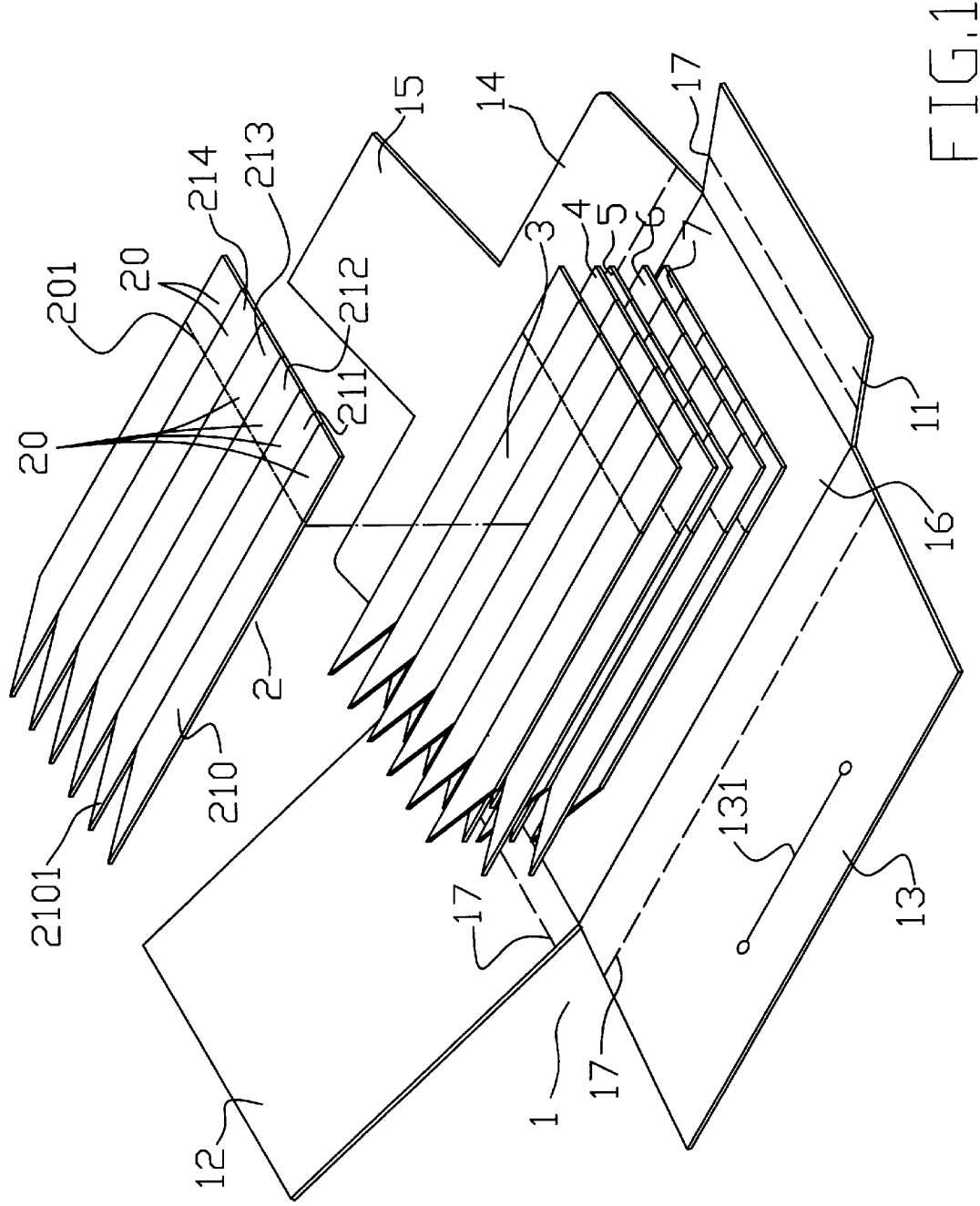
FIG. 1 is an exploded view of the present invention
Figure 2A:
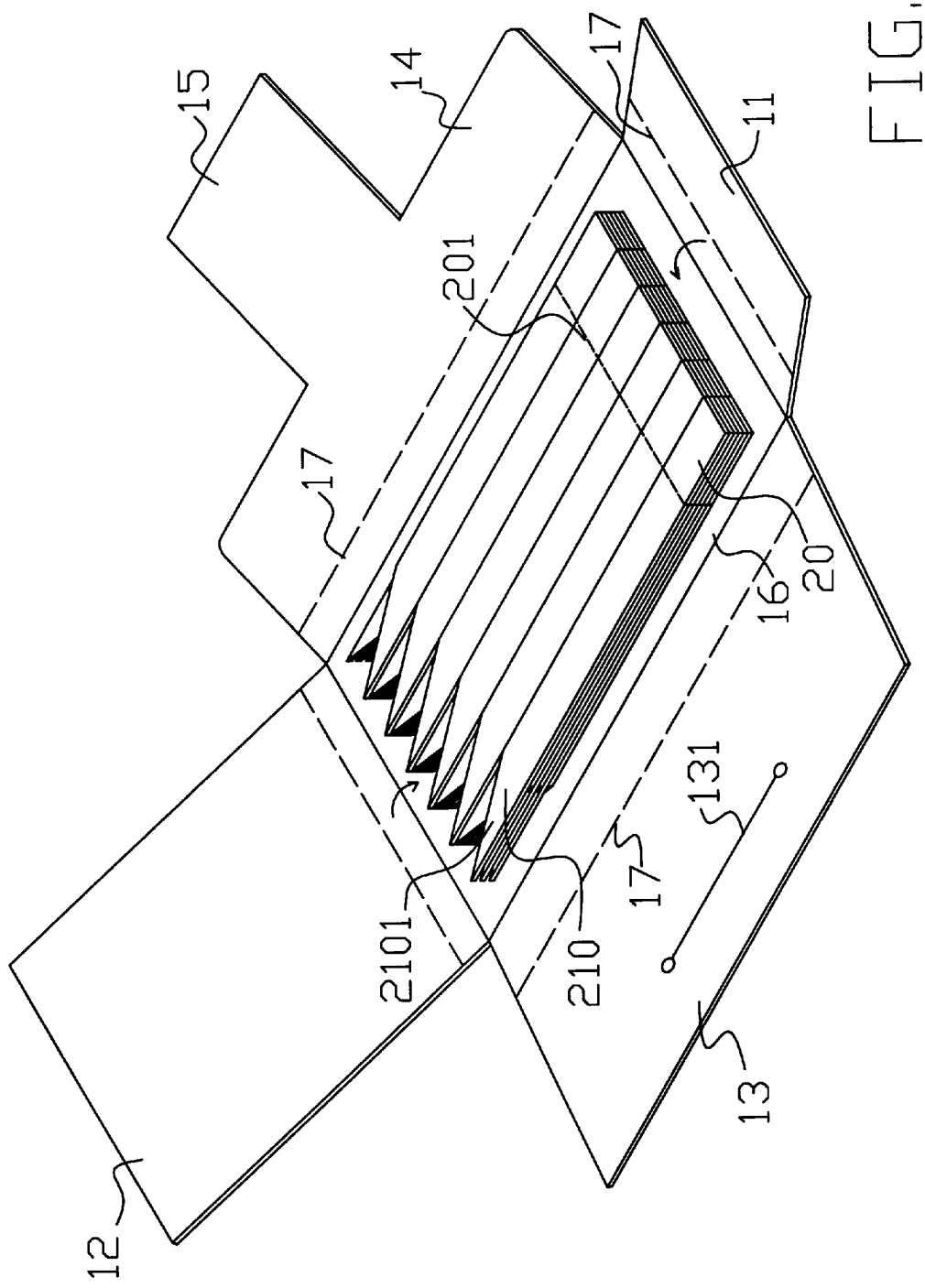
Figure 2C:
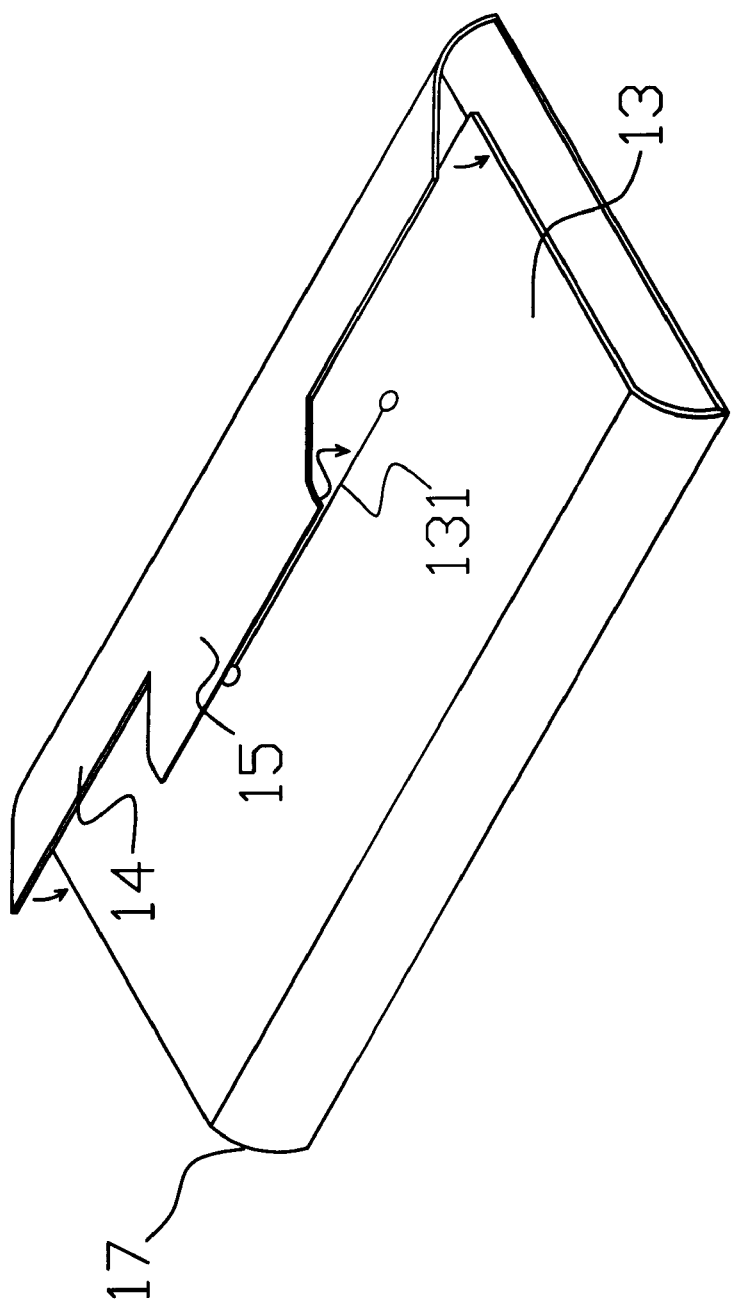
Figure 2D:
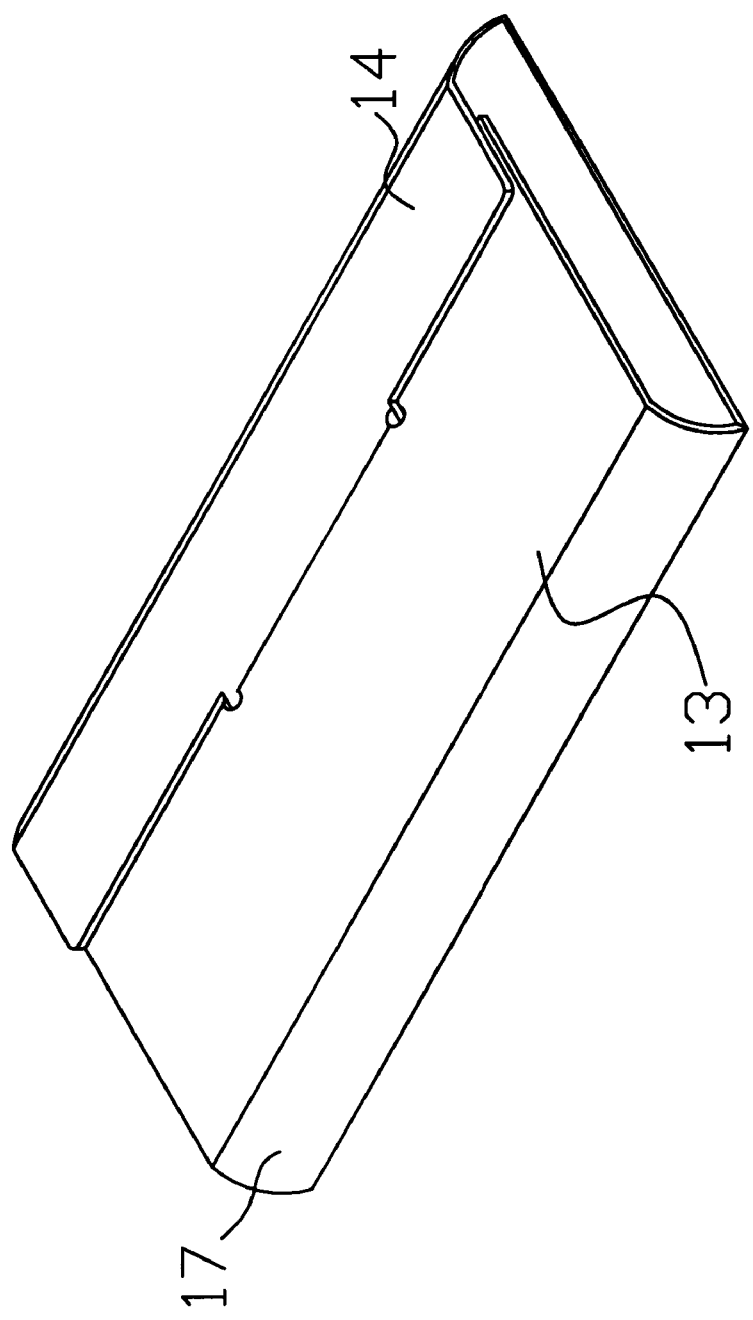

For the purpose of promoting an understanding of the principles of the invention, reference will now be made to the embodiment illustrated in the drawings. Specific language will be used to describe same. It will, nevertheless, be understood that no limitation of the scope of the invention is thereby intended, such alterations and further modifications in the illustrated device, and such further applications of the principles of the invention as illustrated herein being contemplated as would normally occur to one skilled in the art to which the invention relates.

With reference to the drawings and in particular to FIG. 1 thereof, the toothpick assembly according to the present invention generally comprises a plastic envelope 1 and a plurality of toothpick sheets 2, 3, 4, 5, 6 and 7. The plastic envelope 1 is composed of a bottom panel 16, an upper top panel 12, a lower top panel 11, a left panel 13 and a right panel 14. The toothpick sheets 2, 3, 4, 5, 6 and 7 are arranged on the bottom 16 of the plastic envelope 1. The bottom panel 16 of the plastic envelope is rectangular in shape and slightly larger than a business card in size. The upper top panel 12 is rectangular in shape and extends from the front side of the bottom panel 16. The lower top panel 11 is rectangular in shape and extends from the rear side of the bottom panel 16. The left panel 13 is rectangular in shape and extends from the left side of the bottom panel 16 and is formed with a slit 131. The right panel 15 is a T-shaped member extending from the right side of the bottom panel 16. The right panel 14 has a tongue 15 at the outer side configured to engage with the slit 131 of the left panel 13.

Figure 3:
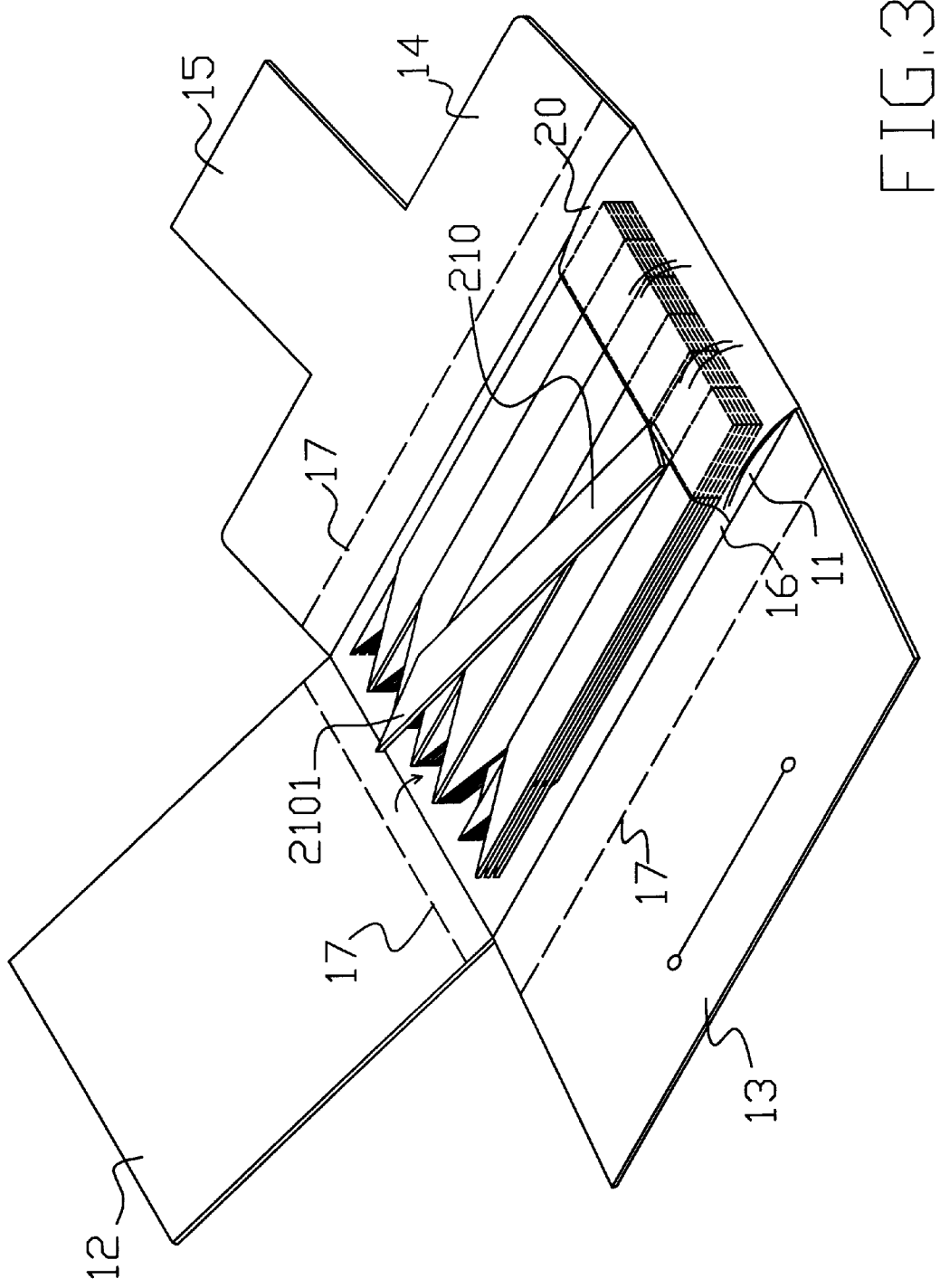
FIG. 3 is a working view of the present invention.
Figure 4:
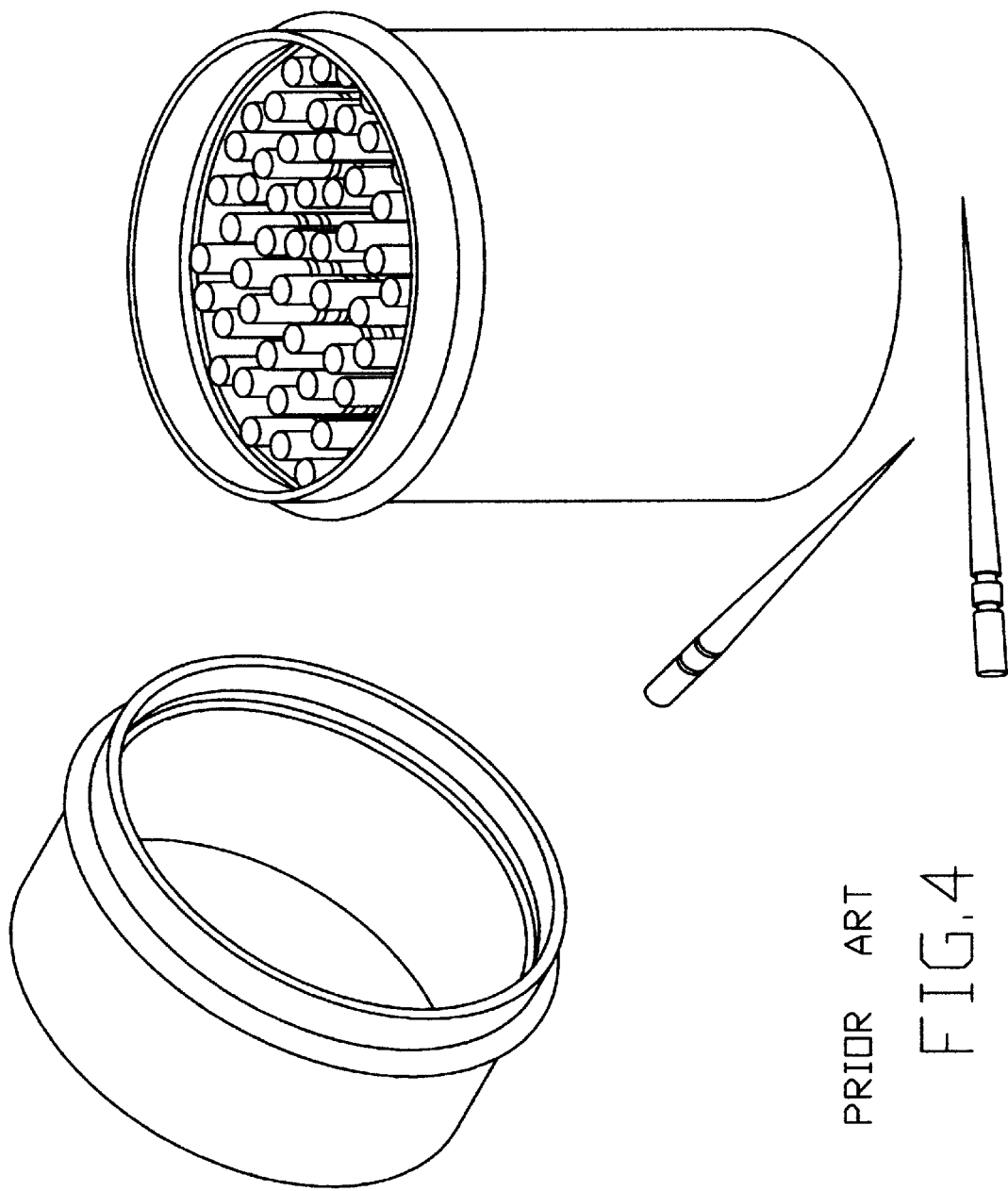
FIG. 4 is an exploded view of a prior art toothpick assembly.

The toothpick sheets 2, 3, 4, 5, 6 and 7 are made of plastic and each formed with six toothpicks 210 separated at the upper portion and joined together at the root portion 20. Further, a breaking line 201 is pressed between the upper portion and the root portion 20 of the toothpick 210 so that the upper portion of the toothpick 210 can be easily broken along the folding line 201 (see FIG. 3). The upper portion of the toothpick 210 has an inclined tip 2101 for cleaning between teeth. The toothpick sheets 2, 3, 4, 5, 6 and 7 are piled up so that their tips 2101 are alternatively arranged in place.

Referring to FIGS. 2A, 2B, 2C and 2D, the toothpick sheets 2, 3, 4, 5, 6 and 7 are first stacked up with their root portions 20 adhered together and their tips alternatively arranged in place. Then, the root portion 20 of the lowermost toothpick sheet is affixed to the bottom panel 16 of the plastic envelope 1. Thereafter, the lower top panel 11 is folded on the toothpick sheets and affixed to the root portion of the uppermost toothpick sheet by adhesive or the like.

Then, the upper top panel 12 is folded on the upper portion of the uppermost toothpick sheet to keep the toothpick sheets from being made dirty and preventing a user from getting injured inadvertently. Thereafter, the left panel 13 is folded on the upper and lower top panels 11 and 12 and then the right panel 14 is folded on the left panel 13 with the tongue 15 inserted into the slit 131 thereby forming a toothpick assembly (see FIG. 2D).

As shown in FIG. 2B, the upper top panel 12, the lower top panel 11, the left panel 13 and the right panel 14 are each provided with a folding line 17 so that they can be folded along the folding lines 17 to form a rectangular container.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A toothpick assembly comprising:

a rectangular plastic envelope having a rectangular bottom, a rectangular upper top panel, a rectangular lower top panel, a rectangular left panel formed with a slit, and a rectangular right panel formed with a tongue configured to fit in said slit; and six plastic toothpick sheets each having six toothpicks separated at an upper portion and joined together at a root portion, a breaking line being pressed between said upper portion and said root portion;

wherein each of said toothpicks has an inclined upper end formed with a pointed tip at an edge thereof, the toothpick tips on each sheet slant in one direction wherein said toothpick tips on every alternate sheet slant in a different direction and said toothpick sheets being stacked up so their tips are alternatively arranged in place and said sheets affixed to the bottom panel of said envelope and each of said upper top panel, lower top panel, left panel and right panel has a folding line.

* * * * *